# United States Patent [19]

Yamamoto et al.

[11] Patent Number: 4,609,656
[45] Date of Patent: Sep. 2, 1986

[54] MEDICAL AGENT FOR IMPROVING AND TREATING MENTAL SYMPTOMS INDUCED BY CEREBRAL DISTURBANCES

[75] Inventors: Minoru Yamamoto, Kanagawa; Masatomi Harada, Saitama, both of Japan

[73] Assignee: Yamanouchi Pharmaceutical Co. Ltd., Tokyo, Japan

[21] Appl. No.: 758,500

[22] Filed: Jul. 24, 1985

[30] Foreign Application Priority Data

Dec. 19, 1984 [JP] Japan .................................. 59-267665

[51] Int. Cl.$^4$ .......................................... A61K 31/535
[52] U.S. Cl. .................................................... 514/239
[58] Field of Search ......................................... 514/239

[56] References Cited

U.S. PATENT DOCUMENTS 4,109,088  8/1978  Murakami et al. .................. 544/174
4,297,356  10/1981  Yamamoto et al. ................ 514/239

Primary Examiner—Stanley J. Friedman
Attorney, Agent, or Firm—Burgess, Ryan & Wayne

[57] ABSTRACT

A medical agent for improving and treating mental symptoms induced by cerebral disturbances comprising a composition containing 2-(7-indenyloxymethyl)morpholine (generic name: indeloxazine) or an acid addition salt thereof as the effective component. Preferred examples of the acid addition salt are the hydrochloride, sulfate, maleate, etc.

5 Claims, No Drawings

MEDICAL AGENT FOR IMPROVING AND TREATING MENTAL SYMPTOMS INDUCED BY CEREBRAL DISTURBANCES

BACKGROUND OF THE INVENTION 2-(7-Indenyloxymethyl)morpholine used as the effective component in this invention is a compound previously reported as possessing an antidepressive activity (see, U.S. Pat. No. 4,109,088). In addition, it was reported that the compound possesses a memory and learning effect and is useful as a memory enhancer, and hence the disclosed use is deemed to be different from that of the medical agent of this invention (cf. U.S. Pat. No. 4,297,356).

DETAILED EXPLANATION OF THE INVENTION

This invention relates to a medical agent for improving and treating mental symptoms induced by cerebral disturbances. More particularly, this invention relates to such agent containing 2-(7-indenyloxymethyl)morpholine (hereinafter referred to as "indeloxazine") or an acid addition salt thereof as the effective component.

Functional disturbances of brain induced by head injury, and cerebrovascular diseases such as cerebral infarction, cerebral hemorrhage, cerebral arteriosclerosis, cerebral thrombosis, induce the various symptoms which appear as sequelae. Disturbance of the region of cerebral lateral lobe or hippocampus induces decrease of intellectual function but most of the cerebral disturbances has the damage of other regions and does not induce decrease of intellectual function. Symptoms without decrease of intellectual function in cerebral disturbances are subjective symptoms such as headache, dizziness, tinnitus, heavy feeling of head, tremor of feet and hands, and mental symptoms. Mental symptoms appear in most of all cerebral disturbances and give pain and difficulty to patients and their family. Target indications of the medical agent of this invention are improvement and therapy of such mental symptoms.

Thus, improving and therapeutic agents of mental symptoms in the case of this invention are effective on decrease of spontaneity and motivation, emotional disturbance, sleep disturbance and abnormal behaviour, which are induced by functional disturbances of brain, and which are symptoms without decrease of intellectual function.

Decrease of spontaneity and motivation means decrease of response (decrease of reactivity), decreased expression of demands (impairment in expression of demands), decreased interest in surroundings, decreased volition in daily activity, and decreased interest in housekeeping, leisure activities, hobbies etc.

Emotional disturbance means poor facial expression, ill humor, anxiety, restlessness, melancholy (depressed mood), emotional incontinence and so on.

Abnormal behaviour means agitation, excitation, tachyphasia, hyperactivity, fugue, delirium and so on.

2-(7-Indenyloxymethyl)morpholine [generic name: indeloxazine] used for the medical agent of this invention may be a free base compound or an acid addition salt thereof. Suitable acid addition salts are the hydrochloride, sulfate, maleate, etc.

The following experiments are shown in order to demonstrate the improving and therapeutic effect of the medical agent of this invention containing indeloxazine hydrochloride on mental symptoms.

EXPERIMENT 1

Facilitatory effects on spontaneous EEG in aged rats (EEG: electroencephalogram).

The effects were tested using Wistar rats (22 months old), each group consisting of 4 rats. Effects of intraperitoneally administered indeloxazine hydrochloride on spontaneous EEG, especially theta wave component (4~7.75 Hz), were observed in rats with electrodes chronically implanted in the cerebral cortex.

The results are shown in the following table 1.

Indeloxazine hydrochloride significantly enhanced the theta wave components and desynchronized the spontaneous EEG in aged rats.

TABLE 1

| Treatment | Administration Dose (mg/kg i.p.) | Theta Wave Appearance Rate (%) | | | |
|---|---|---|---|---|---|
| | | before administration | 30 | 60 (minutes) | 120 |
| Saline (Control) | (0.1 ml/100 g) | 34.3 ± 2.8 | 34.3 ± 3.8 | 34.1 ± 6.4 | 32.3 ± 1.6 |
| Indeloxazine HCl | 10 | 33.4 ± 0.4 | 54.1 ± 4.5* | 55.6 ± 3.5* | 46.0 ± 6.2 |

Each result is the mean ± SE
*This value showed the significant difference from the control value with a risk ratio of 5% when compared with the control groups

EXPERIMENT 2

Facilitatory effects on synchronized spontaneous EEG in rabbits with lesion of the internal capsule in rabbits.

A group consisting of 4 male rabbits weighing about 3 kg was used. The electrodes were chronically implanted in the cerebral cortex of rabbits and the apoplexy models were made by electrical destruction of the internal capsule which is one of the brain regions where cerebrovascular disturbances frequently occur. Seven days after the destruction, the rabbits were offered to the experiments. Indeloxazine hydrochloride was administered intravenously and cumulatively every 60 minutes interval and the evaluation of the drugs was estimated by the EEG change, especially frequently changes of delta wave (2–3.75 Hz), theta wave (4–7.75 Hz) and alpha wave (8–12.75 Hz). The results are shown in the following table 2. Indeloxazine facilitated the synchronized spontaneous EEG induced by electrical lesion of the internal capsule.

TABLE 2

| Treatment | Wave Area | Appearance Rate (%) | | | |
|---|---|---|---|---|---|
| | | time or cumulative administration dose | | | |
| | | 0 | 60 | 120 | 180 |
| Saline | delta | 69.3 ± 9.2 | 68.9 ± 9.0 | 70.0 ± 9.1 | 69.8 ± 7.3 |
| (Control) | theta | 21.7 ± 5.1 | 22.7 ± 5.5 | 20.9 ± 4.2 | 21.7 ± 4.0 |
| | alpha | 5.0 ± 1.9 | 4.9 ± 1.8 | 4.9 ± 1.8 | 5.1 ± 1.7 |
| | | time or cumulative administration dose | | | |
| | | before administration | 1 | 3 | 10 mg/kg (i.v.) |
| Indeloxazine | delta | 62.0 ± 4.0 | 55.8 ± 4.6** | 55.4 ± 4.0** | 53.0 ± 4.8** |
| HCl | theta | 28.3 ± 2.1 | 33.3 ± 2.9* | 33.6 ± 2.5** | 34.9 ± 2.1* |
| | alpha | 6.0 ± 1.4 | 7.2 ± 1.4* | 7.0 ± 1.3* | 7.8 ± 1.8* |

Each result is the mean ± SE
* and ** The values showed the significant difference from the control values with a risk ratio of 5% and 1% respectively when compared with the control values

EXPERIMENT 3

Facilitatory effect on recovery of consciousness in concussive mice.

The effect was tested using ICR male mice (each group consisting of 10 mice) weighing 20-22 g. An acrylate weight weighing 20 g was dropped from about 20-25 cm height through a tube to strike the vertex and concussion was induced in each of mice. Indeloxazine hydrochloride was intravenously or orally administered 10 or 30 minutes (respectively) before the induction of the experimental concussion. Time from the shock up to the onset of spontaneous movement was recorded. The results are shown in the following table 3.

Indeloxazine hydrochloride (3-10 mg/kg i.v., 10-30 mg/kg p.o.) shortened the time from the shock up to the onset of the spontaneous movement and showed the cerebral activating effect.

TABLE 3

| Treatment | Administration Dose (mg/kg) | Administration Route | Time[1] (minutes) |
|---|---|---|---|
| Saline (Control) | | i.v. | 8.0 ± 1.9 |
| Indeloxazine HCl | 1 | i.v. | 6.1 ± 1.5 |
| | 3 | | 2.7 ± 0.8* |
| | 10 | | 1.9 ± 0.5* |
| Saline (Control) | | p.o. | 7.6 ± 1.3 |
| Indeloxazine HCl | 3 | p.o. | 5.5 ± 0.9 |
| | 10 | | 3.7 ± 0.6* |
| | 30 | | 2.6 ± 0.7** |

[1]Time from the shock up to the onset of the the spontaneous movement
*and **The values showed the significant difference from the control values with a risk ratio of 5% and 1% respectively when compared with the control values

EXPERIMENT 4

Enhancing effect on aminergic system in brain.

The effect was tested using male Wistar rats (22 months old) weighing 360-440 g, each group consisting of 8 rats. Drugs (indeloxazine hydrochloride; 10 mg/kg i.p.) were administered to the rats once a day over a period of 3 weeks. The animals were sacrificed by decapitation 60 minutes after the last administration of the drug. The brains (diencephalon and brain stem) were analyzed for serotonin (5-hydroxytryptamine) and norepinephrine levels. The results are shown in the following Table 4.

By the administrations of indeloxazine hydrochloride, there were observed increases of the levels of serotonin and norepinephrine in brain (namely, contents of serotonin and norepinephrine in diencephalon and brain stem).

TABLE 4

| Region | Treatment | Norepinephrine (μg/g tissue) | Serotoin (5-HT) (μg/g tissue) |
|---|---|---|---|
| Diencephalon | Saline (Control) | 1.6511 ± 0.0742 | 1.9498 ± 0.0308 |
| | Indeloxazine HCl (10 mg/kg) | 1.9155** ± 0.0317 | 2.5125*** ± 0.0891 |
| Brain Stem | Saline (Control) | 0.5395 ± 0.0193 | 1.8293 ± 0.0298 |
| | Indeloxazine HCl (10 mg/kg) | 0.6598** ± 0.0234 | 2.2506*** ± 0.0816 |

Each result is the mean ± S.E.
and *The values showed the significant differences from the control values with a risk ratio of 1% or 1.0% when compared with the control groups.

EXPERIMENT 5

Anti-hypoxic action

The action was tested using male ICR mice weighing 22-26 g (each group consisting of 7 rats). A gas mixture of nitrogen and oxygen (96:4) was used to induce hypoxia to mice and survival time of mice was observed. The drugs were administered intravenously or orally 30 minutes before exposure of mixed gas. The results are shown in the following table 5. Indeloxazine hydrochloride significantly prolonged the hypoxia-induced lethality time.

TABLE 5

| Treatment | Administration dose (mg/kg) | Administration route | Lethality time (second) |
|---|---|---|---|
| Saline (Control) | (0.1 ml/10 g) | i.v. | 226 ± 11 |
| Indeloxazine HCl | 1 | i.v. | 379 ± 73 |
| | 3 | | 385 ± 58* |
| | 10 | | 415 ± 70* |
| Pure Water | (0.1 ml/10 g) | p.o. | 224 ± 20 |
| Indeloxazine HCl | 3 | p.o. | 229 ± 36 |
| | 10 | | 356 ± 49* |

TABLE 5-continued

| Treatment | Administration dose (mg/kg) | Administration route | Lethality time (second) |
|---|---|---|---|
| | 30 | | 371 ± 41** |

Each result is the mean ± SE
*and **The values showed the significant differences from the control values with a risk of 5% or 1% when compared with the control groups.

EXPERIMENT 6

Action of increasing glucose level in brain.

The action was tested using male ICR mice weighing 33 g (mean body weight), each group consisting of 7 mice. Drugs (indeloxazine hydrochloride; 2 mg/kg) were administered intraperitoneally once a day over a period of 7 days. 30 minutes after the last administration of the drug, whole bodies of the mice were frozen in liquid nitrogen. The levels (contents) of glucose, lactic acid, ATP, and Creatine phosphate in the whole brain except cerebellum and medulla oblongata were determined. The results are shown in the following table 6. By the administration of indeloxazine hydrochloride, siginificant increase of brain glucose and ATP levels was observed; on the other hand, there was no observed change in the lactic acid level. Thus, it is suggested that indeloxazine hydrochloride possesses an enhancing effect on brain energy metabolism.

TABLE 6

| Treatment | Administration dose | glucose | lactic acid | ATP | Creatine phosphate |
|---|---|---|---|---|---|
| Control | | 1.070 ± 0.066 | 2.709 ± 0.0119 | 2.542 ± 0.137 | 2.134 ± 0.099 |
| Indeloxazine HCl | 2 mg/kg i.p. | 1.461 ± 0.132** | 2.733 ± 0.132 | 2.875 ± 0.043* | 2.214 ± 0.063 |

Each result is the mean ± SE
*and **The values showed the significant differences from the control values with a risk of 5% or 1% when compared with the control groups.

In the above, there are explained novel effects of indeloxazine which are entirely different from other already known effects (antidepressive activity and memory enhancing and learning effect).

Facilitatory effects on spontaneous EEG (results of Experiment 1 and 2) and faciltatory effect on recovery of consciousness (result of Experiment 3) show that indeloxazine possesses an action for activating cerebral function.

It is well known that there appears decrease of spontaneity and motivation in the case of patients with cerebral disturbances.

Further, it is known that there appears synchronized spontaneous EEG in the case of such patients [cf. Gerat. med. 20, 1183-1192 (1982)].

Enhancing effect on aminergic system (result of Experiment 4) shows that indeloxazine possesses an action for increasing the levels of serotonin and norepinephrine in diencephalon and brain stem. It is known that contents of serotonin and norepinephrine are significantly reduced in the brains of patients with cerebral disturbances [Arai H., Kosaka K. and Iizuka R., "Journal of Neurochemistry" 43, 388-393 (1984); Meyer J. S. et al., "Neurology of Aging" (1976) Ed. Ierry and Gershon, Raven Press, New York p 121-138]. Further it is known that emotional disturbance and sleep disturbance are associated with an deficiency of amines (serotonin and norepinephrine). [European Journal of Pharmacology 5, 357-366(1969); Schildkraft J. J. "Psychopharmacology" A Generation of Progress. New York, Raven Press, (1978), P. 1223-1234 and P. 1235-1247; and Electroencephalogr. Clin. Neurophysiol., 25, 481-490(1968)].

By Experiments 5 and 6, anti-hypoxic action and glucose level increasing action of indeloxazine are proved. It is known that there appear decrease of oxygen supply (hypoxic condition) and reduction of brain energy metabolism in the case of patients with cerebral disturbances [cf. Heyman A. et al., The cerebral circulation and metabolism in arteriosclerotic and hypertensive cerebrovascular disease. "New Engl. J. Med., 249, 223-229(1953)]. Further it is also known that hypoxic condition in brain and reduction of brain energy metabolism are associated with reduction of cerebral function, and possibly cause various mental symptoms (decrease of spontaneity and motivation, emotional disturbance, sleep disturbance, etc.) [cf. Psychosomatics 23, 846-853(1982)].

Acute toxicity of indeloxazine hydrochloride is shown below.

Animal—$LD_{50}$ (mg/kg, p.o.)
Mice—above 340 mg/kg
Rats—above 1000 mg/kg

From the above results, it is suggested that indeloxazine or indeloxazine hydrochloride is effective in decreasing spontaneity and motivation, emotional distrubance, sleep disturbance and abnormal behaviour, and has low toxicity; thus the compound is useful for improving and treating mental symptoms caused by cerebral disturbances.

Medical agents containing indeloxazine or an acid addition salt thereof according to this invention (that is, medicaments of this invention containing such compound) may be prepared by conventional methods using conventional carriers or excipients. Medicaments contain indeloxazine or an acid addition salt thereof (e.g. the hydrochloride). They may for example be administered orally as tablet, powder, troche, pills, capsules, granules; parenterally by intravenous or intramuscular injection; suppositories; or other suitable forms for administration in liquid, fluid, or solid state, for example ointment, adhesive tape, plaster, etc. Among them, oral administeration by tablet, powder, granules and capsules are preferable. Conventional carriers or excipients used for the medicaments are non-toxic solid or liquid pharmaceutical materials, and examples thereof are lactose, magnesium stearate, starch, talc, gelatine, agar, pectine, arabia gum, olive oil, sesame oil, cacao butter, ethylene glycol.

One example for the administration as tablet is shown below.

Medical composition:
Formulation for one tablet:
Indeloxazine hydrochloride—10 mg
Lactose—80 mg
Starch—25 mg
Talc—4 mg Magnesium Stearate—1 mg Tablets are prepared by conventional manner after granulation, each tablet weighing 120 mg containing the above components.

The appropriate dose is determined in each case considering factors such as the symptom, age and sex of the patient, but for an adult a daily total of 10 to 200 mg, for oral administration, is usually administered. The medicaments were administered in one to five doses per day.

What is claimed is:

1. A method of improving and treating mental symptoms in a host wherein the mental symptoms are decrease of spontaneity and motivation, emotional disturbance, sleep disturbance and abnormal behavior, which are induced by functional disturbance of the brain, and which are symptoms without decrease of intellectual function, said method comprising administering to said host a pharmaceutically effective amount for improving said mental symptoms, of 2-(7-indenyloxymethyl)morpholine or an acid addition salt thereof and a pharmaceutically acceptable carrier.

2. A method as claimed in claim 1 wherein the mental symptoms are decrease of sponteneity and motivation, sleep disturbance, and abnormal behaviour.

3. A method as claimed in claim 1 wherein the acid addition salt is the hydrochloride, sulfate or maleate.

4. A method as claimed in claim 1 wherein the acid addition salt is the hydrochloride.

5. A method as claimed in claim 1 wherein 2 to 200 mgs of the effective ingredient is administered.

* * * * *